United States Patent [19]

Wolbarsht et al.

[11] Patent Number: 5,267,856
[45] Date of Patent: Dec. 7, 1993

[54] LASER SURGICAL METHOD

[75] Inventors: Myron L. Wolbarsht; Edward D. Gomes, both of Durham, N.C.

[73] Assignee: Premier Laser Systems, Inc., Irvine, Calif.

[21] Appl. No.: 763,350

[22] Filed: Sep. 20, 1991

[51] Int. Cl.$^5$ .............................................. A61C 1/00
[52] U.S. Cl. ..................................... 433/29; 433/215; 606/10
[58] Field of Search ....................... 433/29, 215, 216; 606/3, 10, 13, 15, 16; 128/665

[56] References Cited

U.S. PATENT DOCUMENTS

| | | | |
|---|---|---|---|
| 3,769,963 | 11/1973 | Goldman et al. | 128/665 |
| 3,821,510 | 6/1974 | Muncheryan | 219/121 L |
| 3,910,276 | 10/1975 | Polyanyl | 128/303.1 |
| 4,521,194 | 6/1985 | Myers | 433/215 |
| 4,784,135 | 11/1988 | Blum | 128/303.1 |
| 4,818,230 | 4/1989 | Myers et al. | 433/215 |
| 4,826,431 | 5/1989 | Fujimura | 433/29 |
| 4,940,411 | 7/1990 | Vassiliadis | 433/215 |
| 5,092,864 | 3/1992 | Hayes et al. | 606/10 |

FOREIGN PATENT DOCUMENTS 9011728  10/1990  World Int. Prop. O. ............ 433/215

OTHER PUBLICATIONS

CA-Holloway and Swartz, Jr., The Interaction of Water Vapor with Erbium and Erbium Dideuteride Films, Applied Spectroscopy 31(2):167-168 (1977).
CB-Wolbarsht, Laser Surgery:CO2 or HF, IEEE J. Quantum Electronics QE-2-(12):1427-1432 (1984).
CC-Nelson, Yow, Liaw, Macleay, Zavar, Orenstein, Wright, Andrews, and Berns, Ablation of Bone and Methacrylate by a Prototype Mid-Infrared Erbium:YAG Lasr, Lasers in Surgery and Medicine 8:494-500 (1988).
CD-Hibst and Keller, Experimental Studies of the Application of the Er:YAG Laser on Dental Hard Substances: I. Measurement of the Ablation Rate and II. Light Microscopic and SEM Investigations, Lasers in Surgery and Medicine 9:338-351 (1989).
CE-McKenzie, An Extension of the Three-zone Model to Predict Depth of Tissue Damage beneath ER:YAG and HO:YAG Laser Excisions, Phys. Med. Biol. 34(1):107-114 (1989).
CF-Nelson, Orenstein, Liaw, and Berns, Mid-Infrared Erbium:YAG Laser Ablation of Bone: The Effect of Laser Osteotomy on Bone Healing, Lasers in Surgery and Medicine 9:362-374 (1989).
CG-Walsh, Jr. and Deutsch, Er:YAG Laser Ablation of Tissue: Measurement of Ablation Rates, Lasers in Surgery and Medicine 9:327-337 (1989).
CH-Breguet and Luthy, Transmission of Water under Erbium Laser Irradiation, IEE J. Quantum Electronics 26(2): 207-209 (1990).
CI-Gonzalez, Van De Merwe, Smith and Reinisch, Comparison of the Erbium-Yttrium Aluminum Garnet and Carbon Dioxide Lasers for In Vitro Bone and Cartilage Ablation, Laryngoscope 100:14-17 (1990).
CJ-Hoke, Burkes, Gomes, and Wolbarsht, Erbium:YAG (2.94 um) Laser Effects on Dental Tissues, J. Laser Applications Summer/Fall 1990.

*Primary Examiner*—John J. Wilson
*Attorney, Agent, or Firm*—Olive & Olive

[57] ABSTRACT

A method of ablating or cutting a selected area of a material with a laser, wherein a substance such as water that absorbs the laser radiation is applied to the area in an amount to allow the substance to be absorbed into pores, cracks and other holes in the substance but without pooling on the surface of the material. Application of the substance is done immediately before or during each laser pulse.

8 Claims, No Drawings

LASER SURGICAL METHOD

BACKGROUND OF THE INVENTION

1. Field of the Invention

This invention relates to laser surgery and to cutting of dental and other hard tissue and non-cellular material.

2. Description of the Related Art

Laser use in dental enamel surgery was reported as early as 1964 using a ruby laser. Although such reports indicated that lasers could be used on dental hard tissue, lasers have not generally been used clinically until recently for surgical processes, including drilling teeth, because of the large amount of damage to nearby tissue that is often associated with such drilling. Pulsed eximer lasers as well as lasers producing infrared radiation have, however, been used recently for soft tissue and bone ablation due to the fact that these types of lasers have been found to do less damage than previous lasers.

Myers et al. patented a method for removing decay from teeth using a yttrium-aluminum-garnet (YAG) laser for a picosecond to several milliseconds (U.S. Pat. No. 4,818,230). The laser was used to eradicate tooth decay located in the dentin, "without significantly heating the tooth and thus without damage to the nerve". The disclosure of this patent and all other patents and publications referred to herein is incorporated herein by reference.

A YAG laser has also been used to remove incipient carious lesions and/or stain from teeth (U.S. Pat. No. 4,521,194). This use of a YAG laser was found to slightly fuse the crystals which form the tooth enamel and make the tooth enamel more impervious to decay.

Blum et al. (U.S. Pat. No. 4,784,135) discloses use of an ArF excimer laser as an ultraviolet light source (wavelengths less than 200 nm) to ablatively photodecompose decayed teeth and remove the surrounding enamel.

Erbium is a metallic element of the rare-earth group that occurs with yttrium and is also used as a source of laser irradiation. An Er:YAG laser is a solid-state, pulsed laser which has a maximum emission in the mid-infrared region at 2.94 um. Water absorbs strongly in this region with the water absorption coefficient for radiation produced by an Er:YAG laser being ten times that of radiation produced by a $CO_2$ laser. Laser surgery performed with an Er:YAG laser apparently results in water in the target tissue absorbing radiant energy and heating to boiling to produce water vapor. The water vapor builds up in pressure at the surgical site until a microexplosion occurs and a small portion of tissue is ablated. A number of publications have discussed the great potential for Er:YAG lasers for tissue, bone and cartilage ablation (e.g., Laryngoscope 100:14, 1990; Lasers in Surgery and Medicine 8:494, 1988; 9:327, 1989; and 9:362, 1990). Radiation from a pulsed Er:YAG laser can be transmitted through optical fibers and its pulse nature allows cooling between pulses Researchers in Germany have found that pulsed 2.94 um Er:YAG laser radiation in vitro is effective in removal of both dentin and enamel (Hibst and Keller, Lasers in Surgery and Medicine 9:338, 1989). These researchers found that when the duration of the total erbium laser pulse was about 250 microseconds with a pulse train of single spikes of about 1 microsecond each, roughly cone-shaped holes were produced. They also found that with a radiant exposure of 30 J $cm^{-2}$, the depth hole in dentin and enamel was proportional to the number of pulses, except at higher numbers of pulses for enamel.

In a companion study, the same researchers used light and scanning electron microscopy to view tooth dentin and enamel exposed to Er:YAG laser radiation (Lasers in Surgery and Medicine 9:345, 1989). Using the same laser treatments as in the companion paper, they found that very few charred or fused zones or cracks were found with the Er:YAG treatment, as compared to $CO_2$ laser dental surgery. There was also little heating of the tissue surrounding the crater.

Water has been used in conventional dental surgery and in laser dental surgery as a coolant for the tooth after a surgical pulse. For example, the patent of Vassiliadis et al. (U.S. Pat. No. 4,940,411) discloses a dental laser method using a Neodymium:YAG laser. In this invention, water is sprayed on the tooth after a pulse, followed by drying of the tooth prior to a subsequent activation of the pulsed laser. This patent and the work of others stress the importance of keeping the tooth dry during delivery of the laser pulse, especially for any lasers, such as an Er:YAG laser, productive of radiation that is absorbed by water to minimize heating of and damage to the surface of the tooth.

In contrast to the recited prior practices, the present invention is based on the surprising discovery that controlled addition of water, rather than drying of the surface, prior to and/or during laser surgery, so that no more than a thin film of water is present during surgery, results in a significant increase in laser efficiency and less residual damage than with the prior laser surgery methods for hard materials. In addition, the method of the invention based on the aforesaid discovery results in less heating of the tissue surrounding the surgical site than with prior methods of laser irradiation.

It is therefore an object of this invention to provide a method of laser surgery that results in increased surgical efficiency and decreased damage. It is a further object of this invention to provide a method of laser surgery that may be used for hard tissues such as dentin and enamel as well as other hard organic and inorganic substances Other objects and advantages will be more fully apparent from the following disclosure and appended claims.

SUMMARY OF THE INVENTION

A method of performing laser surgery or cutting a selected area of a hard material such as teeth, bones or noncellular material is disclosed, said material having surface pores in the selected area, said method comprising:

(a) adding a selected liquid to the selected area in a manner and amount so that the selected liquid enters the surface pores or is chemically held in the material at the surface in the selected area but does not remain pooled on the material surface;

(b) irradiating the selected area while the selected liquid is present in the pores using pulses of a laser having radiation which is absorbed by the selected liquid; and (c) repeating steps (a) and (b) until the ablation is terminated with step (a) being performed immediately prior to or during each laser pulse.

It is particularly important to keep the tooth moist with the minimum amount of added water or other absorbent substance.

Thus, in the invention, a radiation absorbent substance such as water is applied to a selected cutting site, preferably as a fine mist. The absorbent substance is infiltrated into the upper porous layer of the selected cutting site so that the absorbent substance infuses into pores and interstices at the site. The water may also be present in a loose chemical combination with the tooth material, or present as water of crystallization. This limited presence of water allows efficient and accurate laser ablation by a laser which produces radiation absorbable by the absorbent substance. When water is used as the absorbent substance, an Er:YAG laser at 2.94 um is particularly effective with a long pulse train.

Other aspects and features of the invention will be more fully apparent from the following disclosure and appended claims.

DETAILED DESCRIPTION OF THE INVENTION AND PREFERRED EMBODIMENTS THEREOF

The present invention is for a method of laser surgery comprising infiltration of water into the surface pores of a selected cutting site. Preferably, the laser used emits a wavelength which is substantially absorbed by water. A preferred laser for use in the invention is an Er:YAG laser because it emits in or near the 3 um region absorption peak for water. Other liquids which can be used with an Er:YAG laser include ethyl alcohol and various glycols. Thus, as used herein the terms "water" and "moisture" and related terms include any substances which absorb at the wavelength of the particular laser. Radiation absorbent substances to use with an Er:YAG laser preferably have an OH group with high absorption in the 3 um region of the spectrum. Although erbium:YAG is mentioned above as a preferred laser for use in the invention, the invention herein clearly contemplates use of other lasers having an emission wavelength at about 2.9 um. Thus, for example, a hydrogen fluoride (HF) laser having a wavelength of about 2.95 works with water as the absorbing substance. The invention also includes other liquids or radiation absorbent substances having other absorption peaks which may be used in the method of the invention with other lasers emitting in or near the corresponding absorption region for these substances.

The method of the invention is preferably used on materials of a generally fibrous or granular structure where there are pores, interstices, micro-cracks, channels or other types of generally very small openings between the hard components of the materials at the site where the laser cutting is to be done. The materials may also have sites where the absorbing liquid may be chemically held by being combined with chemical components of the material and/or by being present in the form of water of crystallization. For ease of reference, these openings in the materials and the mean of the absorbing substance being chemically held are referred to together herein as "pores". Such materials include bone, teeth, enamel, dentin, ceramics, and earthenware and are generally low in moisture content at the site to be exposed to laser radiation, particularly after the initial laser irradiation at the site.

In the method of the invention, water is applied to the surface of the material immediately before or during laser irradiation. The word "surface" as used here means the initial tooth surface prior to laser ablation or the newly formed surface of the material from previous laser ablation step(s) to which one or more subsequent laser pulses will be directed. Thus, an Er:YAG laser pulse train of a length of about 250 microseconds (us) may be used, with about a 14 us recycle time and each pulse being about 2.5 us in length.

The method of the invention requires that the water, or whatever liquid or radiation absorbent substance is used must infiltrate into the pores of the selected cutting site without forming a barrier to penetration of the laser radiation into the material surface. The location and amount of liquid in the pores of the material must also give the material a high absorption coefficient at each laser exposure.

According to the method of the invention, the water or other radiation absorbent substance is applied to the material by being sprayed in the form of a mist on to the surface of the material at the selected site for laser irradiation, or the radiation absorbent substance is flowed on to the material from a location adjacent to the selected site. It is important that water not be pooled on the surface of the selected site because laser radiation is absorbed and does not penetrate such a pool, cannot act effectively on the substance to be cut, and results in undesirable heating. Thus, adding water with an eye dropper, without removing excess water, results generally in decreased laser efficiency. To maintain water in the pores of the material at the surgical site throughout the irradiation procedure, water is misted on to the surface between laser pulses and may be continued during the pulses, so long as it does not produce surface pooling. A directed jet of water can be used which is then blown off by a puff of moistened air. Dry air should not be used to blow off excess water unless care is taken to be sure water remains in the pores which is generally difficult to ascertain in clinical practice. Any other methods which allow the surface pores to be hydrated, for example, wicking moisture on to the tooth from a moisture source, without leaving any standing water on the surface are within the scope of the present invention.

The laser beam may be transmitted from a laser generator known in the art and may be focused by any means known in the art. Although certain practical limitations exist in the maximum energy output of an Er:YAG laser, the wavelength emitted by this type laser can be transmitted through optical fibers to the selected cutting or surgical site.

To expose a site to laser energy according to the invention, the instrument and irradiation parameters including power level and duration of exposure are adjusted by means known in the art for the desired size of ablation or cutting. For dental surgery these parameters are preferably adjusted so that the damage zone is no greater than 5 um. If the tissue is not properly hydrated as with the method of the invention and if the pulse rate is too great (e.g., greater than 1/second) the damage zone size increases and the quality of ablation suffers. The invention allows excellent cutting in a small damage zone by absorption of the laser radiation by, or hydration of, the tooth or other material.

In summary, in addition to a source of laser irradiation, the method of the invention requires a source of the liquid mist or spray or other means of applying liquid.

The features and advantages of the present invention will be more clearly understood by reference to the following examples, which are not to be construed as limiting the invention.

EXAMPLES

Example I

Non-carious human incisor, canine and pre-molar teeth are extracted and stored in saline solution Details of this procedure are found in Hoke et al., J. Laser Applications (Summer-Fall 1990) (published Oct. 1, 1990), pages 61–65, the disclosure of which is incorporated herein. Prior to surgery, the teeth are fixed to a graduated mobile stage which is calibrated for precise movement in three dimensions. A binocular microscope is used to select the surgical site. Laser energy produced by an Er:YAG laser (Schwartz Electro-Optics, Inc., Model ER3000) and in the free running long pulse mode (2.5 microsecond individual pulses, 14 microsecond cycle time, 250 microsecond train length) is focused with a biconvex lens (FL 150 mm) and a mirror to the selected site.

As the experimental teeth are subjected to laser irradiation, a water mist produced by an air-water syringe is simultaneously applied to the surgical site. Control teeth are subjected to laser irradiation without application of a water mist. Thermocouples (Mallinckrodt Hi-Lo Temp., Type T made by Mallinckrodt, Inc.) are imbedded in tooth-colored filling material placed in the pulp chambers of the teeth and are attached to a digital temperature monitor. This temperature monitor has a resolution of 0.1° C. at three displays per second. Temperature is monitored during pulsed irradiation at energy levels of 118, 116, 95, 60 and 56 mJ per pulse train.

As enamel and dentin ablation is produced and observed, each tooth is moved slowly in order to produce typical cavity preparations on the occlusal and cervicofacial tooth surfaces. The starting temperature and the temperature at the ablation level are recorded at each energy level.

EXAMPLE II

As shown below in the results of laser irradiation according to Example I, utilization of the water mist results in only a small rise in temperature.

TABLE 1

| Pulse Energy (mJ) | Pulse No. | Start Temp. (°C.) | End Temp. (°C.) | Max Temp. (°C.) |
|---|---|---|---|---|
| 95 | 0–569 | 22.4 | 23.5 | 23.5 |
| (6 pulses/sec) | 569–1650 | 24.3 | 25.4 | 25.5 |
|  | 0–1566 | 20.6 | 25.7 | 26.2 |
|  | 1566–2079 | 25.7 | 29.1 | 29.1 |
| 60 | 0–2964 | 22.6 | 19.8 | 24.4 |
| (8 pulses/sec) | 2964–4645 | 19.8 | 22.7 | 22.7 |
|  | 4645–8397 | 22.7 | 24.3 | 24.3 |
| 56 | 0–2440 | 20.3 | 21.3 | 21.3 |
| (10 pulses/sec) | 2440–2990 | 19.7 | 20.7 | 20.7 |

The average temperature rise in the pulp in the experimental teeth as measured by the thermal probe is 2.2° C. At a pulse energy of 95 mJ, (6 pulses per second) the total temperature change is 6.6° C. in about 10 minutes; at 60 mJ (8 pulses per second), the increase is only 1.7° C. in 17 minutes; and at 56 mJ (10 pulses per second), the increase is only 1.3° C. in 2440 pulses.

In the control teeth, when water is not added and teeth are subjected to 58 mJ (10 pulses per second), the temperature rise is greater than 20° C. in 1023 pulses.

Example III

Teeth prepared according to Example I are sectioned and ground. The samples to be used for scanning electron microscopy are dehydrated and then sputter-coated with gold and palladium using methods known in the art for scanning electron microscopy. A scanning electron microscope is used to observe the surface at the interface of the natural tooth and the cavity and to observe intracravity enamel and dentin walls.

When observed with light and electron microscopy, the ground sections of teeth show that enamel ablation has occurred producing grooves, flakes, shelves, pits and craters as appropriate for dental surgery, with little effect on underlying enamel and dentin. The teeth treated according to the invention have a generally smooth appearance, being more smooth than teeth drilled with a diamond drill. The control teeth show little ablation and have melting of the enamel and no visible change in the pulp chamber.

Example IV

Examples I–III are repeated with other hard materials having small pores or other openings, including bone, ceramic and earthenware materials. Efficient and low temperature removal of the hard material at the selected site is also seen with these materials.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of ablating a selected area of a material with a laser, said material having a surface and surface pores in the selected area, said method comprising:
    (a) adding a selected liquid to the selected area in a manner and amount so that the selected liquid enters the surface pores or is chemically held in the material at the surface in the selected area but does not remain pooled on the material surface;
    (b) irradiating the selected area while the selected liquid is present in the pores using pulses of a laser having radiation which is absorbed by the selected liquid; and
    (c) repeating steps (a) and (b) until the ablation is terminated with step (a) being performed immediately prior to or during each laser pulse.

2. A method of ablating a selected area according to claim 1, wherein the selected liquid is water and the laser is an erbium:YAG laser.

3. A method of ablating a selected area according to claim 2, wherein the water is applied as a mist.

4. A method of ablating a selected area according to claim 2, wherein the water is applied as a directed jet of water and any pooled water in the selected area is driven off by blowing moistened air at the selected area.

5. A method of ablating a selected area according to claim 2, wherein the material is a tooth.

6. A method of ablating a selected area of a material with a laser, said method comprising:
    (a) adding a selected liquid to the selected area in a manner and amount so that the selected liquid is spread in a thin layer on the surface in the selected area but does not remain pooled on the surface; and (b) irradiating the selected area while the selected liquid is present on the surface using pulses of a laser having radiation which is absorbed by the selected liquid, wherein the selected liquid is water and the laser is an erbium:YAG laser.

7. A method of ablating a selected area of a material with a laser, said method comprising:
(a) adding a selected liquid to the selected area in a manner and amount so that the selected liquid is spread in a thin layer on the surface in the selected area but does not remain pooled on the surface; and
(b) irradiating the selected area while the selected liquid is present on the surface using pulses of a laser having radiation which is absorbed by the selected liquid, wherein the liquid is water which is applied as a mist.

8. A method of ablating a selected area of a material with a laser, said method comprising:
(a) adding a selected liquid to the selected area in a manner and amount so that the selected liquid is spread in a thin layer on the surface in the selected area but does not remain pooled on the surface; and
(b) irradiating the selected area while the selected liquid is present on the surface using pulses of a laser having radiation which is absorbed by the selected liquid, wherein the liquid is water which is applied as a directed jet and any pooled water in the selected area is driven off by blowing moistened air at the selected area.

* * * * *